(12) United States Patent
Sauska et al.

(10) Patent No.: US 7,388,219 B2
(45) Date of Patent: Jun. 17, 2008

(54) FLUORESCENT LAMP WITH OPTIMIZED UVA/UVB TRANSMISSION

(75) Inventors: Christian Sauska, Fairfield, CT (US); Arpad Pirovic, Woodbridge, CT (US)

(73) Assignee: Lightsources, Inc., Orange, CT (US)

( * ) Notice: Subject to any disclaimer, the term of this patent is extended or adjusted under 35 U.S.C. 154(b) by 0 days.

(21) Appl. No.: 11/405,272

(22) Filed: Apr. 17, 2006

(65) Prior Publication Data

US 2007/0023708 A1 Feb. 1, 2007

Related U.S. Application Data

(60) Provisional application No. 60/672,174, filed on Apr. 15, 2005.

(51) Int. Cl.
*H01J 61/44* (2006.01)

(52) U.S. Cl. .................................. 250/504 R; 313/487
(58) Field of Classification Search ............ 250/504 R; 313/487
See application file for complete search history.

(56) References Cited

U.S. PATENT DOCUMENTS

| | | | |
|---|---|---|---|
| 4,499,403 A | | 2/1985 | Leppelmeier et al. |
| 4,843,279 A | * | 6/1989 | Rattray et al. ............... 313/487 |
| 4,859,903 A | | 8/1989 | Minematu et al. |
| 4,959,551 A | * | 9/1990 | Schlitt ..................... 250/504 R |
| 4,967,090 A | * | 10/1990 | Schlitt ..................... 250/504 R |

\* cited by examiner

*Primary Examiner*—David Vanore
(74) *Attorney, Agent, or Firm*—Perman & Green, LLP

(57) ABSTRACT

A low iron soda glass is combined with a UVA phosphor to provide increased uvb transmission from a florescent lamp which may be used as a tanning lamp.

9 Claims, 17 Drawing Sheets

Soda Lime Glass Tubing                                                                                           SG81

Introduction

SG81 glass is a soda lime silicate. This glass is formulated to seal to the lead glasses used in stems and exhaust tubes, for example, SG10 and SG12.

Applications

It is available as tubing used in fluorescent lamps. This glass is also available in a variety of machine blown shapes used in incandescent lamps, electron tubes, ornaments, vacuum bottles, and lighting fixture glassware such as chimneys, shades, and globes.

Physical Properties

Mechanical:
- Density: 2.47 g/cm$^2$
- Young's Modulus: $7.2 \times 10^2$ kg/mm$^2$ ($12.7 \times 10^4$ psi)
- Poisson's Ratio: .22
- Shear Modulus: $3.0 \times 10^4$ kg/mm$^2$ ($5.1 \times 10^4$ psi)
- Knoop Hardness: 465

Viscosity:
- Working Point: 1013°C
- Softening Point: 696° ± 5°C
- Annealing Point: 514° ± 5°C
- Strain Point: 473°C Thermal Expansion:
- Coef. of Exp. ($\times 10^{-7}$/°C): 93.5
- Room Temp/S.P. ($\times 10^{-7}$/°C): 104

Expansion mismatch
- with SG-10: 160 ppm less
- with SG-12: 80 ppm less

Optical:
- Index of Refraction: 1.51
- Birefringence Constant: $\frac{227 \text{ (nm/cm)}}{\text{(kg/mm}^2\text{)}^{-1}}$ Electrical:
- Log. Volume Resistivity
  - @ 250°C: 6.4 Ω cm
  - @ 350°C: 5.1 Ω cm
- Loss Tangent @ 20°C: 1.0%
- Dielectric Constant @ 20°C: 7.33

Key Properties: softening point, anneal point and expansion are controlled within specified tolerances to insure a compatible sealing glass. The values given for the other properties are typical, however, the deviation from these values would be small since composition must be held very precisely to maintain the control of the key properties.

Typical Chemical Composition

| | |
|---|---|
| SiO$_2$ | 73% |
| Al$_2$O$_3$ | 1% |
| Na$_2$O | 17% |
| MgO | 4% |
| CaO | 5% |

Availability:

Standard length drawn tubing and fluorescent tubing.

Packaging

| Size | Tolerance | Out of Round |
|---|---|---|
| T-8 (1.010") | ±.015" | .015" |
| T-12 (1.480") | ±.015" | .015" |
| T-14 1/2 (1.826") | ±.030" | .030" |

Note: T-8 and T-12 fluorescent tubing is normally supplied with an All Points in wall thickness of .029" to .035" and T-14 1/2 a wall of .035" to .043".

| Length | Pieces/Pallet |
|---|---|
| T-8 | |
| 13.8" to 19.9" | 4320 |
| 21.0" to 21.9" | 2160 |
| 22.0" to 35.0" | 2266 |
| 46.8" to 92.8" | 1701 |
| T-12 | |
| 13.8" | 3402 |
| 16.8" to 22.8" | 2268 |
| 23.0 to 46.8" | 1134 |
| 52.8" to 92.8" | 864 |
| T-14 1/2 | |
| All sizes | 504 |

FIG. A1

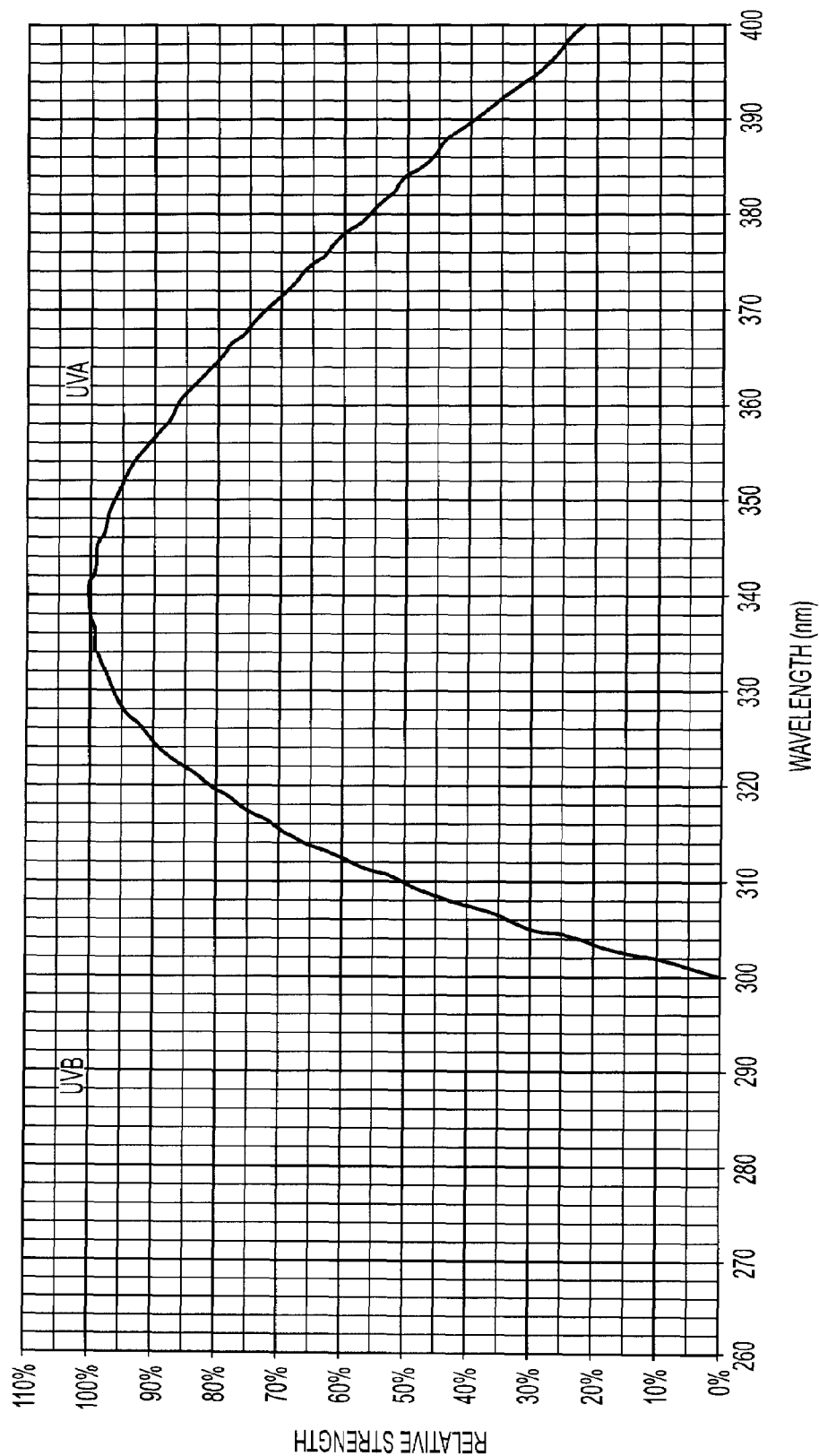
FIG. B1

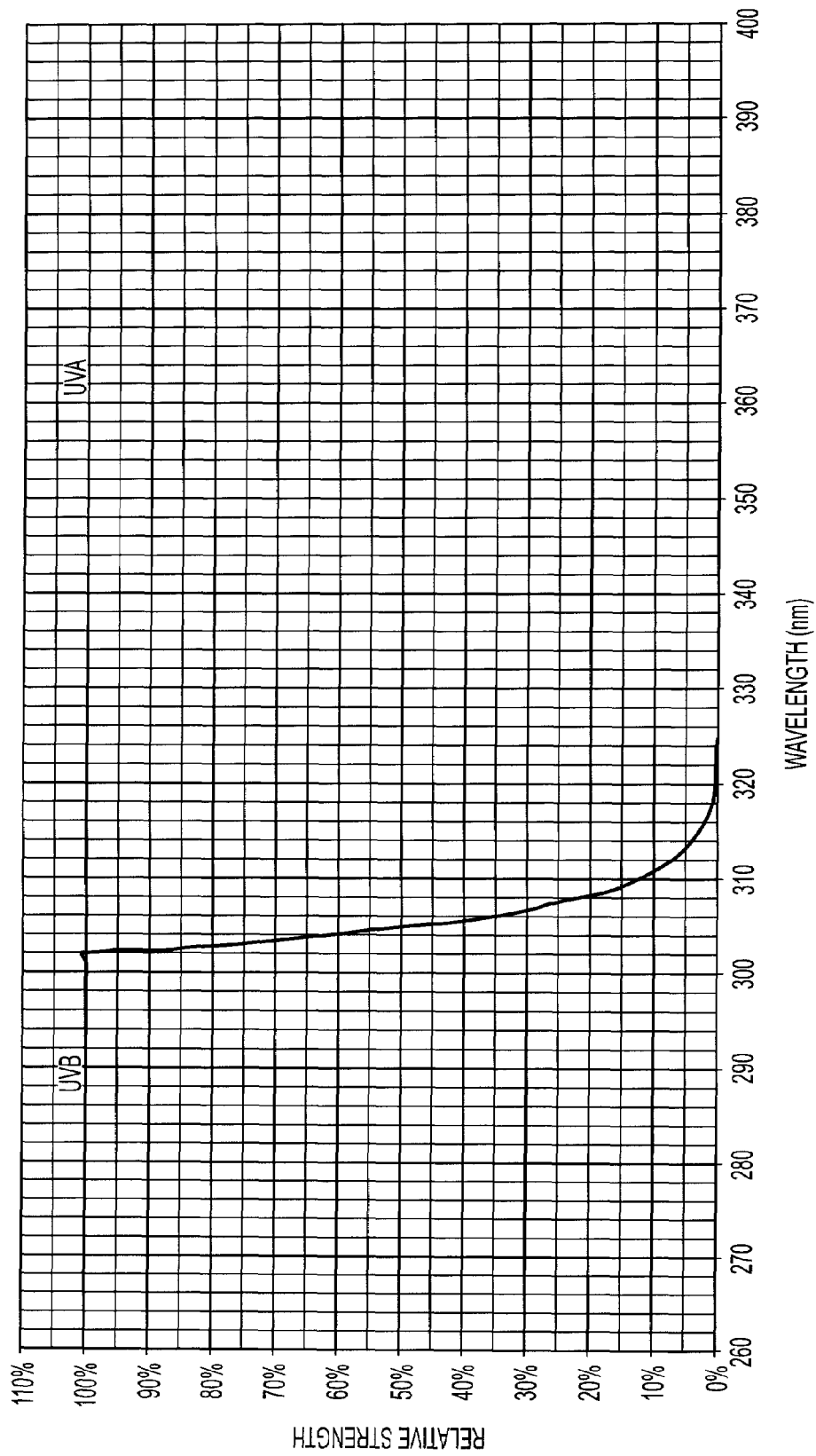
FIG. B2

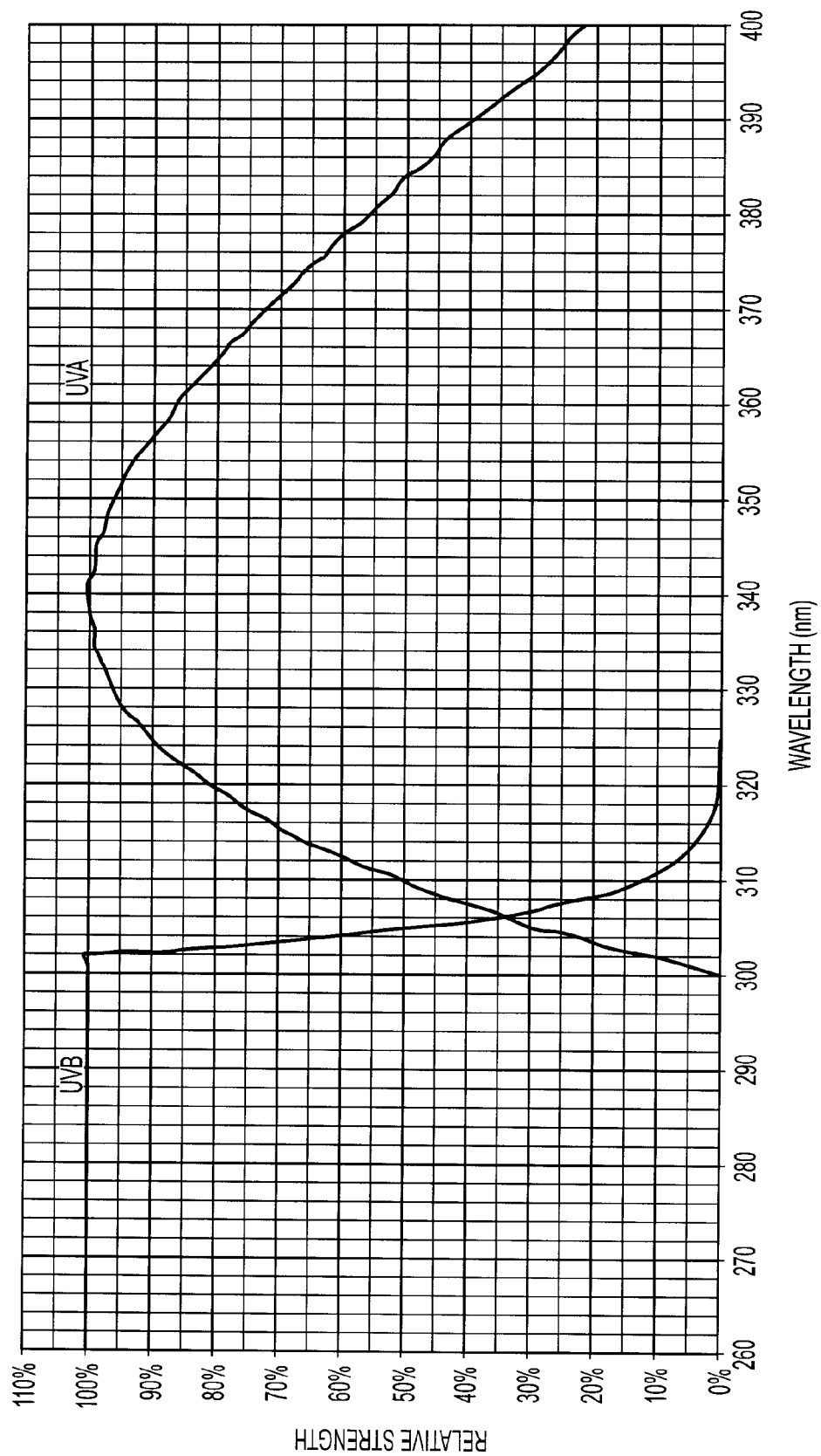
FIG. B3

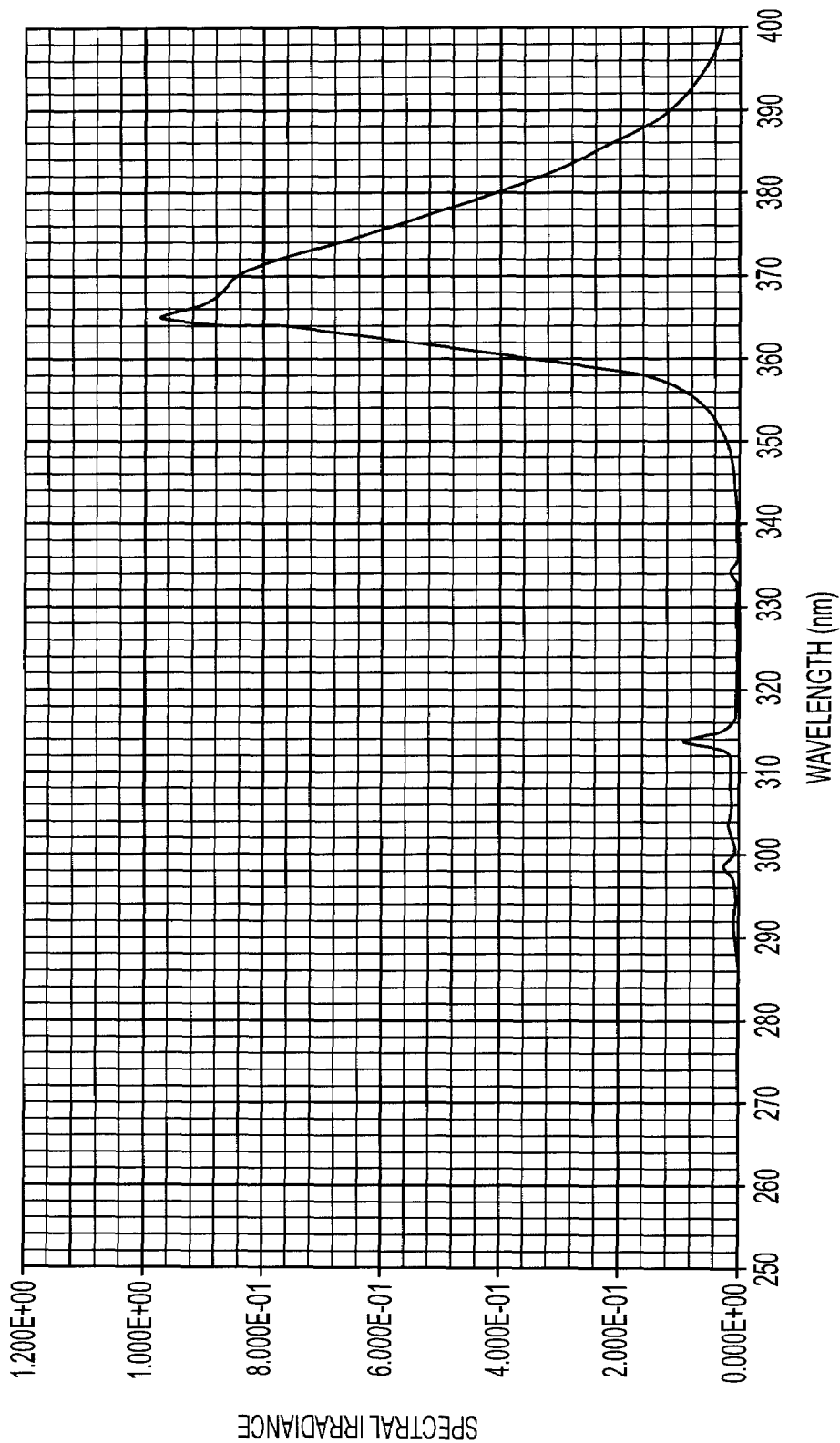
FIG. E1

```
DATA FILE NAME:
DATA FILE DESIGNATION:    951-SOL-GLASS [NP803 6%] [NP802 94%] -VHO-REFLECTOR
DATA FILE UNITS:          IRRADIANCE [(W/cm^2nm))/A]
DATA FILE DATE:           50114
WAVELENGTH RANGE:         250    nm   -   400    nm   AT   1    nm
```

| SUNLAMP RAW DATA (OVER RANGE: 250-400nm AT 1 nm) |

| 250nm | 1.00E-10 | 280nm | 1.27E-07 | 310nm | 1.03E-06 | 340nm | 5.12E-07 | 370nm | 8.31E-06 | 400nm | 1.78E-06 |
|---|---|---|---|---|---|---|---|---|---|---|---|
|  | 2.93E-10 |  | 1.44E-07 |  | 1.14E-06 |  | 5.31E-07 |  | 7.95E-05 |  |  |
|  | 2.10E-09 |  | 1.44E-07 |  | 3.35E-06 |  | 5.53E-07 |  | 7.41E-05 |  |  |
|  | 2.29E-08 |  | 1.80E-07 |  | 9.18E-06 |  | 8.09E-07 |  | 6.89E-05 |  |  |
|  | 4.02E-08 |  | 2.07E-07 |  | 2.35E-06 |  | 8.66E-07 |  | 6.29E-06 |  |  |
|  | 3.16E-06 |  | 2.45E-07 |  | 1.06E-06 |  | 8.05E-07 |  | 5.74E-05 |  |  |
|  | 3.33E-10 |  | 2.98E-07 |  | 9.76E-07 |  | 9.83E-07 |  | 5.14E-05 |  |  |
|  | 0.00E+00 |  | 3.32E-07 |  | 9.36E-07 |  | 1.21E-06 |  | 4.62E-05 |  |  |
|  | 2.29E-10 |  | 4.10E-07 |  | 9.16E-07 |  | 1.58E-06 |  | 4.13E-06 |  |  |
|  | 0.00E+00 |  | 6.76E-07 |  | 8.71E-07 |  | 2.06E-06 |  | 3.87E-05 |  |  |
| 260nm | 1.49E-11 | 290nm | 7.07E-07 | 320nm | 8.78E-07 | 350nm | 2.77E-06 | 380nm | 3.21E-05 |  |  |
|  | 0.00E+00 |  | 5.02E-07 |  | 8.70E-07 |  | 3.75E-06 |  | 2.67E-05 |  |  |
|  | 0.00E+00 |  | 5.52E-07 |  | 8.38E-07 |  | 5.12E-06 |  | 2.51E-05 |  |  |
|  | 2.84E-10 |  | 6.05E-07 |  | 6.27E-07 |  | 6.84E-06 |  | 2.21E-05 |  |  |
|  | 2.05E-09 |  | 6.03E-07 |  | 6.32E-07 |  | 9.27E-06 |  | 1.93E-05 |  |  |
|  | 1.07E-08 |  | 6.54E-07 |  | 7.91E-07 |  | 1.23E-05 |  | 1.69E-05 |  |  |
|  | 6.76E-09 |  | 1.20E-06 |  | 7.57E-07 |  | 1.62E-05 |  | 1.48E-05 |  |  |
|  | 4.15E-10 |  | 2.20E-06 |  | 7.46E-07 |  | 2.14E-05 |  | 1.28E-05 |  |  |
|  | 6.58E-10 |  | 7.71E-07 |  | 7.40E-07 |  | 2.70E-05 |  | 1.12E-05 |  |  |
|  | 1.81E-09 |  | 7.58E-07 |  | 8.87E-07 |  | 3.36E-05 |  | 9.68E-06 |  |  |
| 270nm | 3.55E-09 | 300nm | 8.00E-07 | 330nm | 8.70E-07 | 360nm | 4.11E-05 | 390nm | 8.38E-06 |  |  |
|  | 4.04E-09 |  | 9.02E-07 |  | 8.35E-07 |  | 5.01E-05 |  | 7.21E-06 |  |  |
|  | 6.94E-09 |  | 1.41E-06 |  | 8.17E-07 |  | 8.13E-05 |  | 6.11E-06 |  |  |
|  | 9.79E-09 |  | 1.18E-06 |  | 7.11E-07 |  | 8.87E-05 |  | 5.24E-06 |  |  |
|  | 1.91E-08 |  | 9.21E-07 |  | 1.45E-06 |  | 7.74E-05 |  | 4.48E-06 |  |  |
|  | 4.96E-08 |  | 9.32E-07 |  | 6.88E-07 |  | 9.82E-05 |  | 3.83E-06 |  |  |
|  | 4.31E-08 |  | 9.60E-07 |  | 5.40E-07 |  | 9.38E-05 |  | 3.30E-06 |  |  |
|  | 3.68E-08 |  | 9.73E-07 |  | 5.30E-07 |  | 8.91E-05 |  | 2.82E-06 |  |  |
|  | 5.05E-08 |  | 9.81E-07 |  | 5.12E-07 |  | 8.74E-05 |  | 2.74E-06 |  |  |
|  | 7.48E-06 |  | 1.01E-06 |  | 5.08E-07 |  | 8.58E-05 |  | 2.07E-06 |  |  |

FIG. E2

```
DATA FILE NAME:
DATA FILE DESIGNATION:    951-SOL-GLASS [NP803 6%] [NP802 94%] -VHO-REFLECTOR
DATA FILE UNITS:          IRRADIANCE [(W/cm^2nm))/A]
DATA FILE DATE:           50114
WAVELENGTH RANGE:         250   nm   -   400   nm   AT   1   nm
```

| SUNLAMP CALCULATIONS (OVER RANGE: 250 - 400 nm AT 1 nm) |
|---|

| MAXIMUM EXPOSURE TIMES: |
|---|

```
    MAXIMUM ERYTHEMAL TIME Te:                   52.98 MINUTES
    MAXIMUM MELANOGENIC TIME Tm:                176.24 MINUTES
    FIRST WEEK MAX TIME .75MED Ti:                9.93 MINUTES
```

| IRRADIANCE RATIOS: |
|---|

```
    UVB/UVA PERCENTAGE (RATIO):                   2.53%
```

| TOTAL UV VALUES: |
|---|

```
    TOTAL UVA:                                   17.57
    TOTAL UVB:                                    0.44
```

FIG. E3

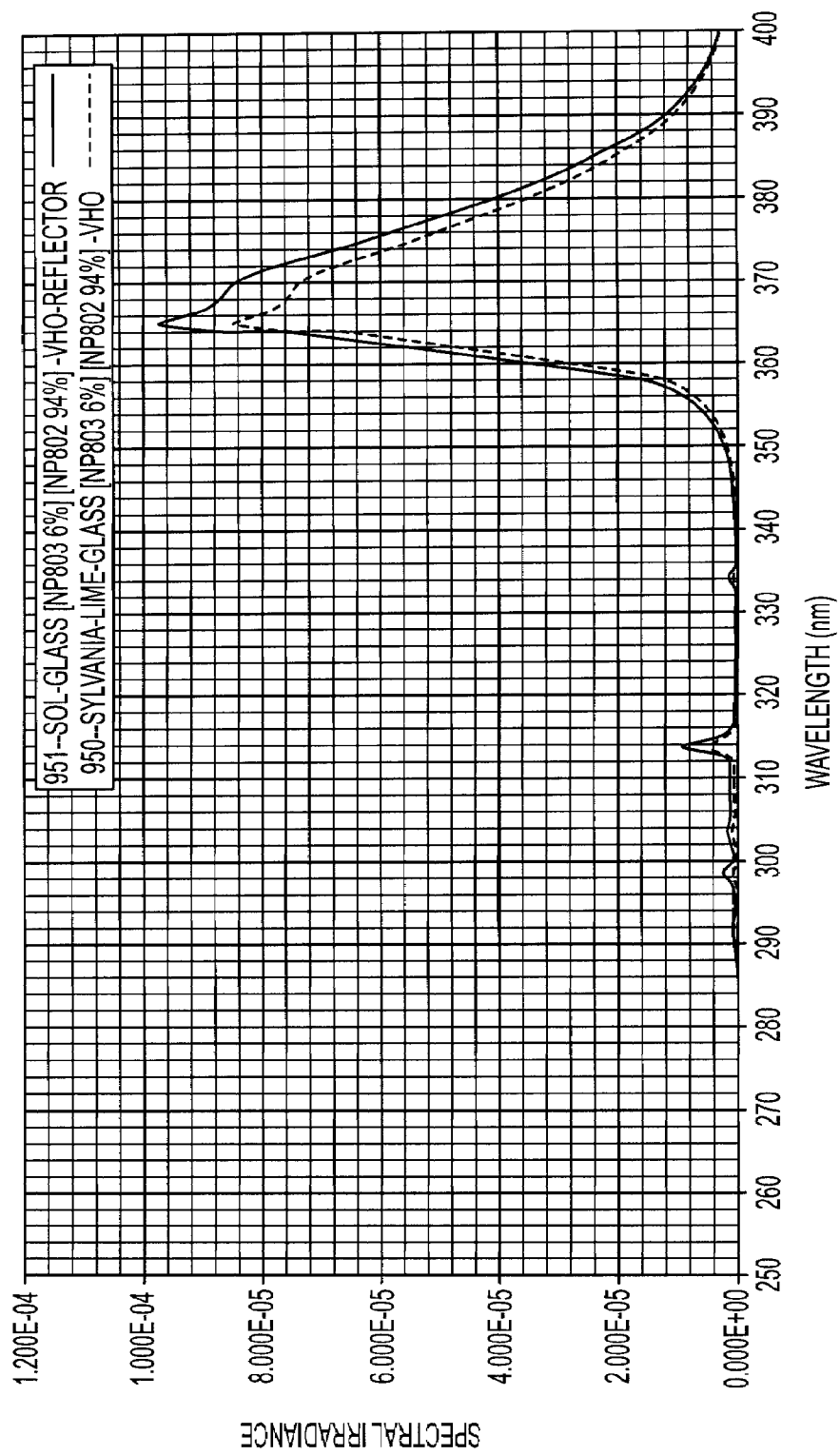
FIG. E4

```
DATA FILE NAME:
DATA FILE DESIGNATION:    950-SYLVANIA-LIME-GLASS [NP803 6%] [NP802 94%] -VHO-REFLECTOR
DATA FILE UNITS:          IRRADIANCE [(W/cm^2nm))/A]
DATA FILE DATE:           50114
WAVELENGTH RANGE:         250    nm   -   400    nm   AT   1    nm
```

| SUNLAMP RAW DATA (OVER RANGE: 250-400nm AT 1 nm) |

| 250nm | 1.00E-10 | 280nm | 8.71E-09 | 310nm | 4.96E-07 | 340nm | 3.97E-07 | 370nm | 7.46E-06 | 400nm | 1.67E-06 |
|---|---|---|---|---|---|---|---|---|---|---|---|
|  | 4.29E-11 |  | 1.12E-08 |  | 5.68E-07 |  | 4.02E-07 |  | 7.20E-06 |  |  |
|  | 0.00E+00 |  | 1.32E-08 |  | 1.63E-06 |  | 4.27E-07 |  | 6.73E-05 |  |  |
|  | 1.86E-09 |  | 1.66E-08 |  | 4.48E-06 |  | 4.70E-07 |  | 6.28E-06 |  |  |
|  | 4.40E-09 |  | 2.04E-08 |  | 1.30E-06 |  | 5.30E-07 |  | 5.73E-06 |  |  |
|  | 4.06E-10 |  | 2.77E-08 |  | 6.06E-07 |  | 6.29E-07 |  | 5.22E-06 |  |  |
|  | 0.00E+00 |  | 3.50E-08 |  | 5.67E-07 |  | 7.59E-07 |  | 4.69E-06 |  |  |
|  | 2.23E-10 |  | 4.23E-08 |  | 5.65E-07 |  | 9.58E-07 |  | 4.19E-06 |  |  |
|  | 0.00E+00 |  | 5.62E-08 |  | 5.53E-07 |  | 1.23E-06 |  | 3.78E-06 |  |  |
|  | 0.00E+00 |  | 9.96E-08 |  | 5.42E-07 |  | 1.63E-06 |  | 3.33E-06 |  |  |
| 260nm | 0.00E+00 | 290nm | 1.13E-07 | 320nm | 5.59E-07 | 350nm | 2.19E-06 | 380nm | 2.93E-06 |  |  |
|  | 5.02E-11 |  | 9.12E-08 |  | 5.63E-07 |  | 3.00E-06 |  | 2.62E-05 |  |  |
|  | 1.43E-11 |  | 1.09E-07 |  | 5.36E-07 |  | 4.05E-06 |  | 2.30E-06 |  |  |
|  | 0.00E+00 |  | 1.27E-07 |  | 5.51E-07 |  | 5.49E-06 |  | 2.02E-06 |  |  |
|  | 0.00E+00 |  | 1.36E-07 |  | 5.61E-07 |  | 7.47E-06 |  | 1.77E-05 |  |  |
|  | 3.33E-10 |  | 1.57E-07 |  | 5.39E-07 |  | 9.95E-06 |  | 1.55E-06 |  |  |
|  | 3.50E-10 |  | 2.88E-07 |  | 5.23E-07 |  | 1.31E-05 |  | 1.36E-05 |  |  |
|  | 3.21E-11 |  | 5.39E-07 |  | 5.18E-07 |  | 1.74E-05 |  | 1.17E-06 |  |  |
|  | 0.00E+00 |  | 2.19E-07 |  | 5.20E-07 |  | 2.22E-05 |  | 1.03E-05 |  |  |
|  | 0.00E+00 |  | 2.31E-07 |  | 4.99E-07 |  | 2.80E-05 |  | 6.87E-06 |  |  |
| 270nm | 1.12E-10 | 300nm | 2.50E-07 | 330nm | 4.80E-07 | 360nm | 3.42E-05 | 390nm | 7.70E-06 |  |  |
|  | 1.56E-10 |  | 3.03E-07 |  | 4.58E-07 |  | 4.19E-05 |  | 6.60E-06 |  |  |
|  | 5.08E-10 |  | 4.72E-07 |  | 4.52E-07 |  | 5.20E-05 |  | 5.62E-06 |  |  |
|  | 5.13E-10 |  | 4.33E-07 |  | 5.01E-07 |  | 5.92E-05 |  | 4.83E-06 |  |  |
|  | 6.90E-09 |  | 3.58E-07 |  | 9.84E-07 |  | 6.88E-05 |  | 4.13E-06 |  |  |
|  | 2.16E-09 |  | 3.83E-07 |  | 5.10E-07 |  | 6.44E-05 |  | 3.54E-06 |  |  |
|  | 2.44E-09 |  | 4.04E-07 |  | 4.04E-07 |  | 8.27E-05 |  | 3.03E-06 |  |  |
|  | 1.76E-09 |  | 4.28E-07 |  | 4.01E-07 |  | 7.90E-05 |  | 2.82E-06 |  |  |
|  | 2.76E-09 |  | 4.52E-07 |  | 3.91E-07 |  | 7.81E-05 |  | 2.27E-06 |  |  |
|  | 5.02E-09 |  | 4.75E-07 |  | 3.89E-07 |  | 7.71E-05 |  | 1.93E-06 |  |  |

FIG. E5

```
DATA FILE NAME:
DATA FILE DESIGNATION:    950-SYLVANIA-LIME-GLASS [NP803 6%] [NP802 94%] -VHO-REFLECTOR
DATA FILE UNITS:          IRRADIANCE [(W/cm^2nm))/A]
DATA FILE DATE:           50114
WAVELENGTH RANGE:         250    nm   -   400   nm   AT   1   nm

SUNLAMP CALCULATIONS (OVER RANGE: 250 - 400 nm AT 1 nm)

MAXIMUM EXPOSURE TIMES:

MAXIMUM ERYTHEMAL TIME Te:              179.32 MINUTES
     MAXIMUM MELANOGENIC TIME Tm:            553.50 MINUTES
     FIRST WEEK MAX TIME .75MED Ti:           33.62 MINUTES

IRRADIANCE RATIOS:

UVB/UVA PERCENTAGE (RATIO):              1.17%

TOTAL UV VALUES:
     TOTAL UVA:                               15.52
     TOTAL UVB:                                0.18
```

FIG. E6

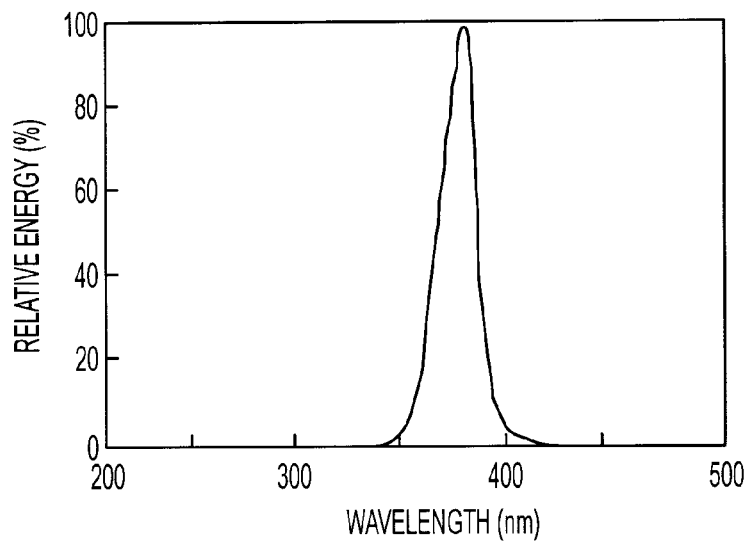
FIG. P1

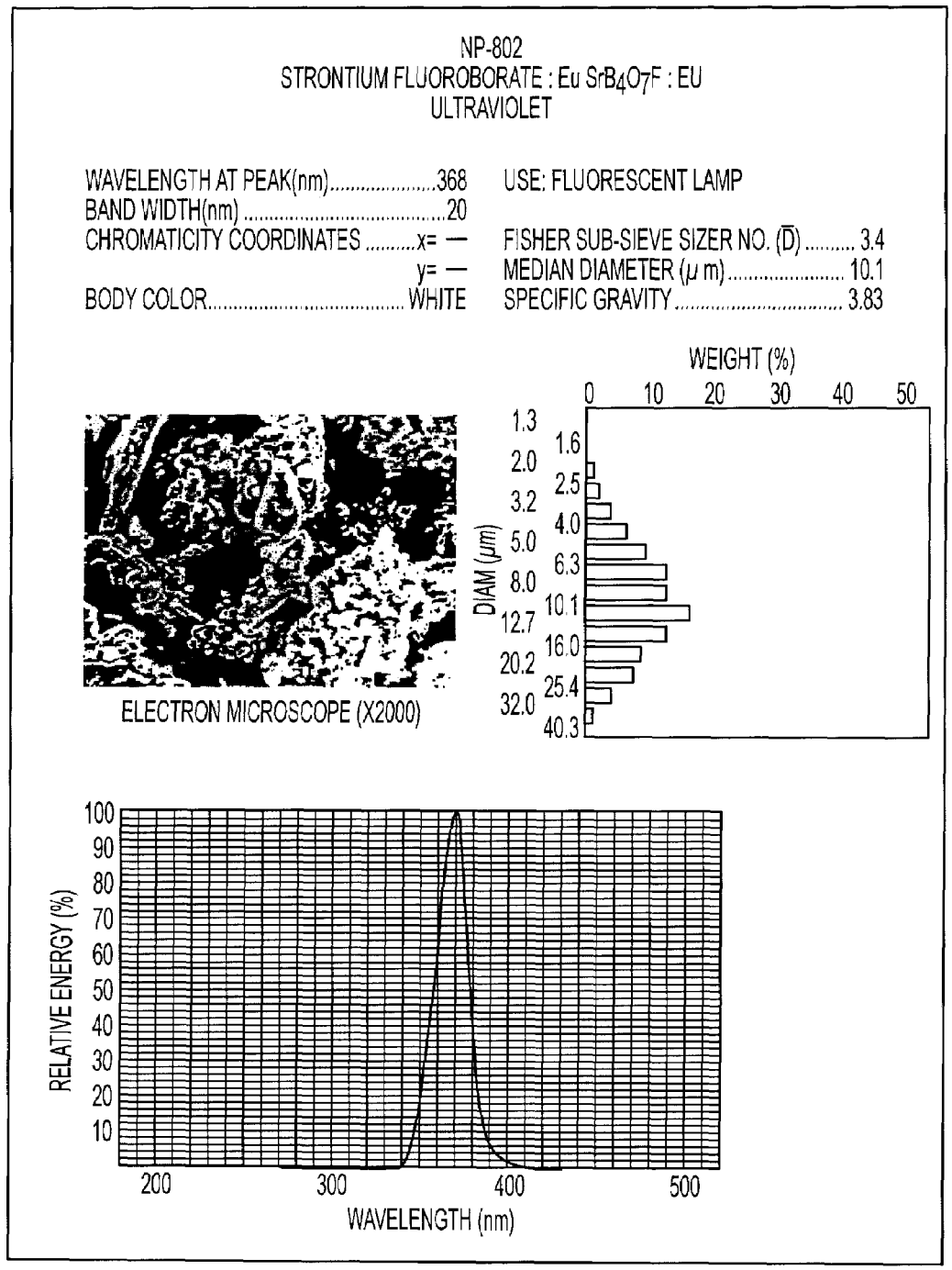
FIG. P2

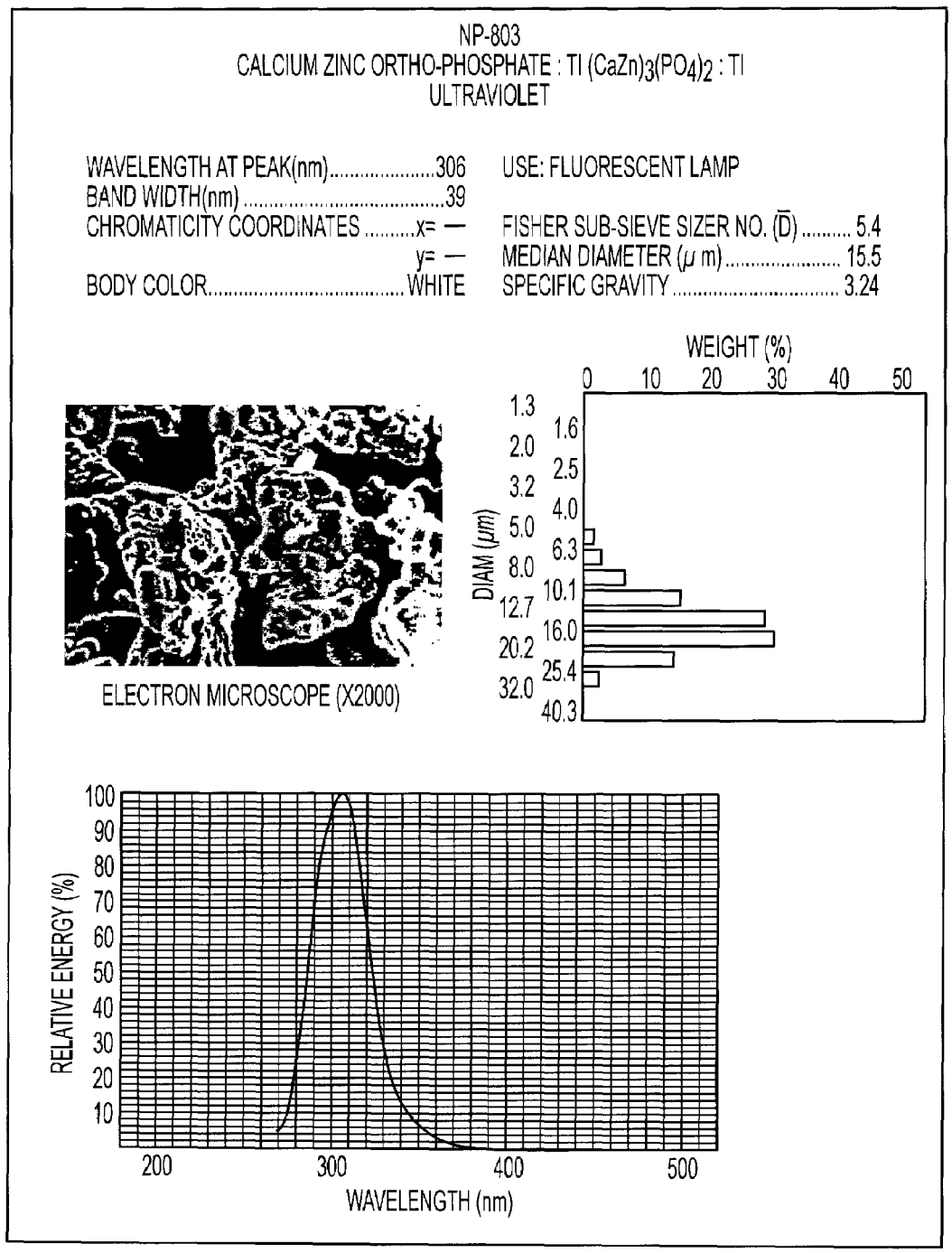
FIG. P3

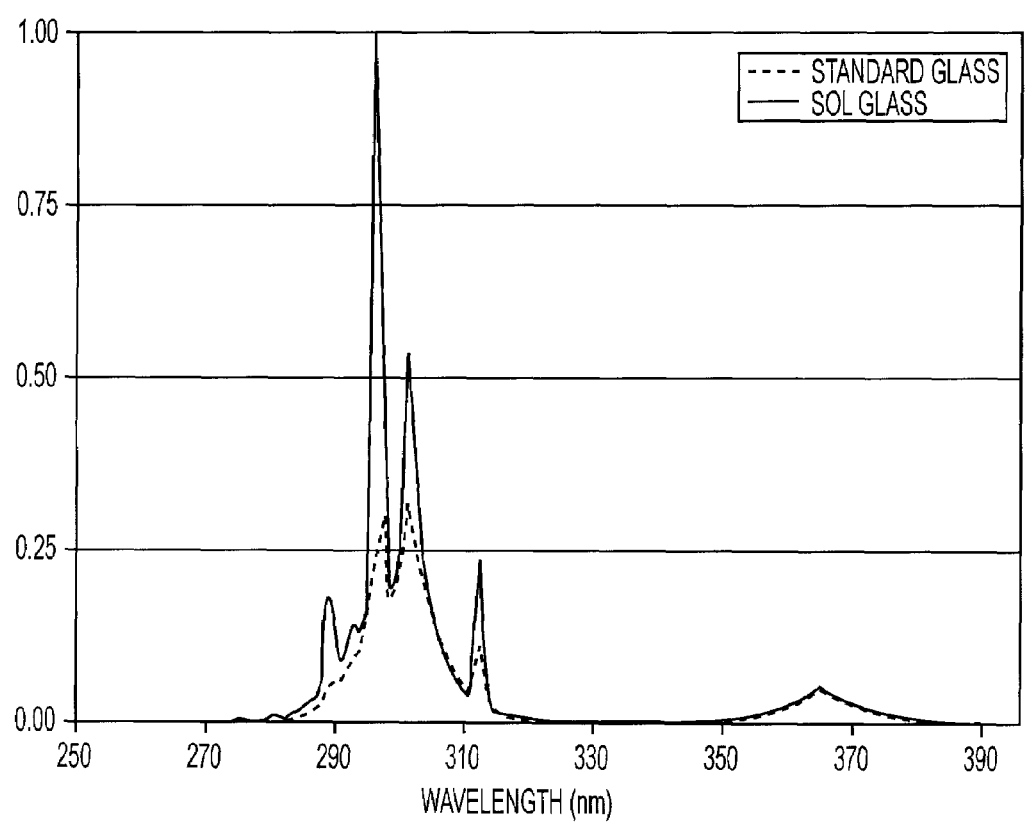
FIG. P4

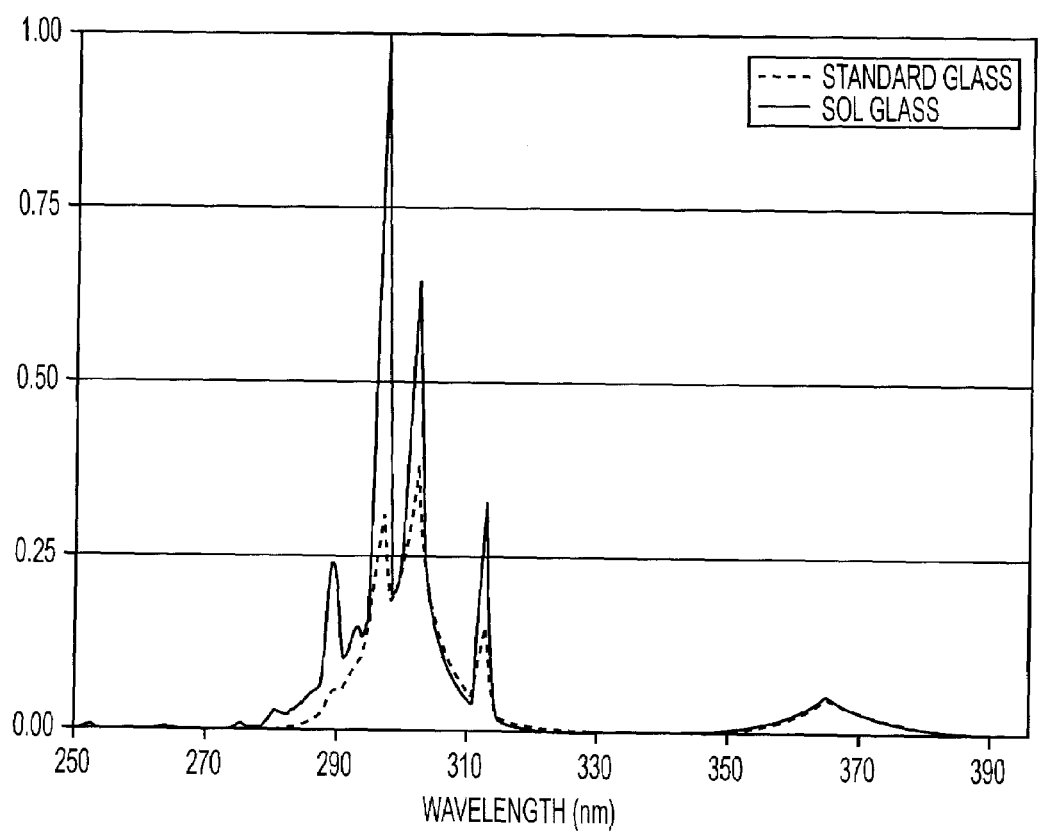
FIG. P5

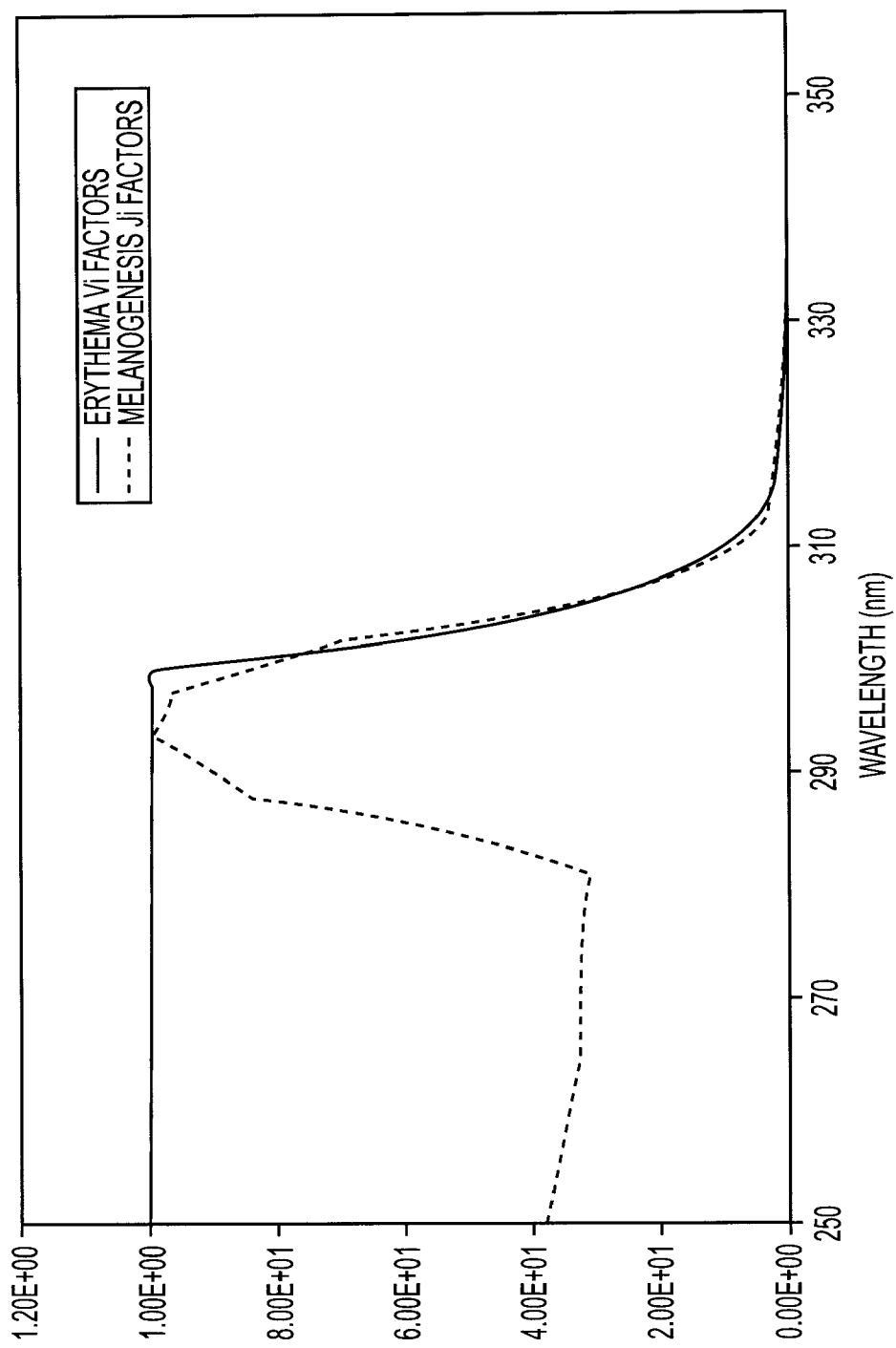
FIG. P6

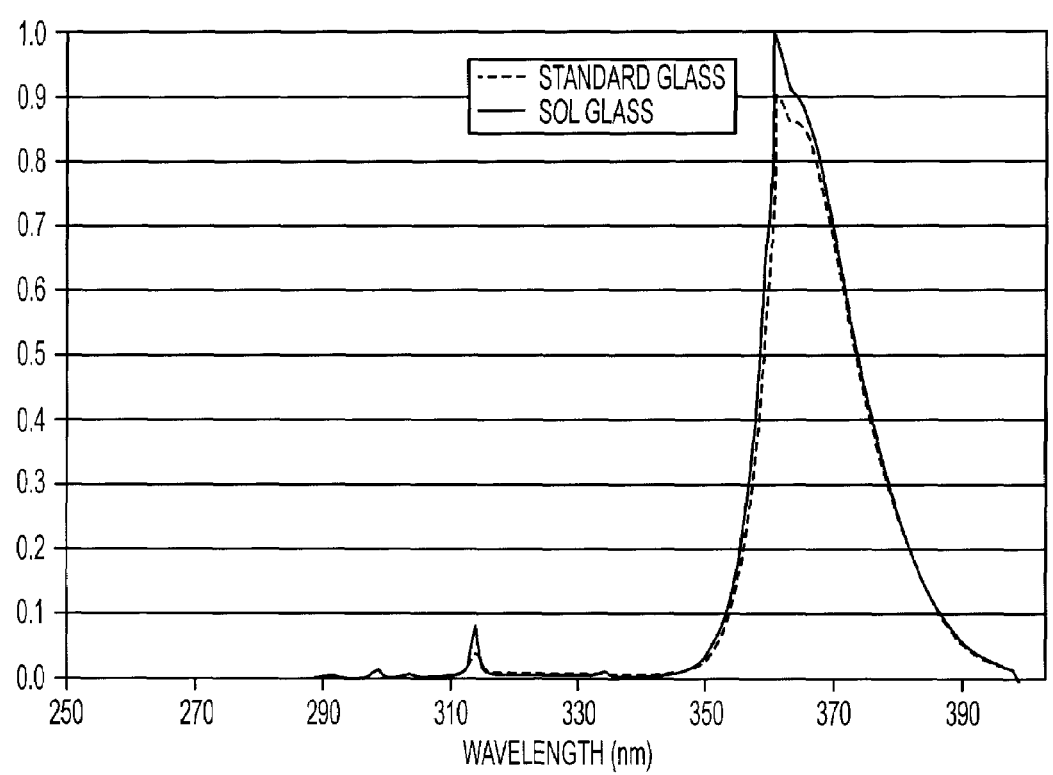
FIG. P7

FLUORESCENT LAMP WITH OPTIMIZED UVA/UVB TRANSMISSION

This application claims priority of U.S. Provisional Patent Application No. 60/672,174, filed Apr. 15, 2005.

BACKGROUND OF THE INVENTION

1. Field of the Invention

The present invention generally relates to an ultraviolet fluorescent lamp, and in particular to an ultraviolet fluorescent lamp used for suntanning.

2. Brief Description of Related Developments

Tanning is generally described as the darkening of one's skin through exposure to ultraviolet (UV) radiation. A person's skin reacts to UV radiation exposure. The reaction is generally dependent upon, for example, the amount of melanin pigment already in the skin naturally and the capability of the person's skin to produce additional melanin (facultative pigmentation).

Melanin is the dark pigment found in the retina, hair and skin, except for the palms of the hands, soles of the feet and lips. Without the protection afforded by the melanin pigment, a person's skin would burn when exposed to UV radiation. The skin includes naturally occurring melanin pigment and produces additional melanin. Melanin is produced by special cells called melanocytes, which are located deep within the outer layer of the skin. When the melanocytes are stimulated by ultraviolet light, they utilize the amino acid tyrosine to produce the melanin pigment. Since the melanin pigment is only able to absorb ultraviolet light of approximately 260-320 nanometers, UVB radiation is need to achieve melanin production. UVA radiation, which has a wavelength of approximately 320-400 nanometers, can promote the production of melanin, but only when there is enough photosensitizing material already in the skin to trigger a UVB reaction. With the presence of UVB, melanocytes are stimulated to divide, creating more pigment cells. During this time, the epidermis thickens to form additional protection, a condition referred to as acanthosis.

In the beginning stages of melanin production, the skin has very little melanin or radiation protection capabilities. As a result, UVA radiation is not blocked by melanin pigments and, due to its longer wavelength, penetrates the skin deeper than UVB, causing damage to the corium. Damage to this layer of the epidermis hastens aging and destruction of collagen and connective tissue. A UVA burn can cause serious damage because it is not felt due to its deep penetration.

Erythema is redness of the skin caused by increased blood flow to the capillaries. There are many causes and manifestations of erythema, one of the more frequent being photosensitivity. Photosensitivity is the reaction of the skin in response to the sun and tends to occur when an infection or a medication increases a person's sensitivity to ultraviolet radiation. Excessive sun exposure increases the risk for erythema multiforme.

Symptoms of Erythema multiforme include fever, itching of skin, a sudden outbreak of spots, bumps, and lesions, typically on knees, elbows, palms, hands, feet, and mouth.

In order for the pigmentation process to be effective, melanin granules must be oxidized or darkened, which requires a high dose of long-wave UVA. Consequently, exposure to UVB radiation functions to create melanin pigment, while UVA exposure ensures the oxidation of the pigment. Together, the proper combined UV exposure operates to create a light-protection mechanism.

As can be seen from FIGS. B1-B3, the relative strength of UVB is significantly diminished at wavelengths greater than approximately 305 nanonmeters.

Various types of glasses are used for tanning lamps. The two main glass types are "soft" glass and "hard" glass. In these cases, the terms "soft" and "hard" refer to the temperature needed to work them. "Hard" glasses contain relatively high percentages of silicon dioxide and/or aluminum or boric oxides. Fused quartz is a hard glass that is pure or almost pure silicon dioxide. Hard glasses can transmit a significant amount of UV radiation but are harder to work because of working temperatures that range from 1100 to 1600° C. Soft glass can be worked at a relatively low temperature (900° C.), and has a wide plastic range over which it can be worked. Fluorescent lamps, neon signs and most incandescent lamps used in the home are soft glass.

Typical soft glasses are soda-lime glass and lead glass. On example of a soda lime glass tubing is described as SG81 glass, which is a soda lime silicate. A product data sheet is attached hereto as FIG. A1.

Tanning lamps are made of a specially formulated soft glass that has much better transmission of ultraviolet ("UV") in the UVA and UVB regions. A standard Osram Lime Glass is generally known to have a 50% UVB transmission characteristic at approximately 305 nanometers. One example of the formation of a UV absorbing lamp glass can be found in U.S. Pat. No. 5,350,972 to Bucher et. al., filed on May 25, 1993, the disclosure of which is incorporated herein by reference and made a part hereof.

It is an objective of the present invention to produce an ultraviolet transmitting lamp that provides enhanced transmission in the UVB range, and preferably in the range of approximately 283 to 305 nanometers.

BRIEF SUMMARY OF THE INVENTION

The present invention generally relates to a unique glass (bulb) formation process and design, resulting in a glass with improved transmission in the UVB region. When the glass of the present invention is used in combination with a unique UVA/UVB phosphor mix, the UV output provides a peak transmission and output in the UVB region, which would be otherwise attenuated using a standard glass. The present invention also relates to a suntanning application using the unique glass design of the present invention in combination with the unique phosphor mix.

Embodiments of the present disclosure utilize a UVA phosphor, that when used in combination with the glass of the present invention, provides increased UV output in the UVB range, and particularly in the range of 283-305 nm, as illustrated for example in FIGS. P4 and P5.

BRIEF DESCRIPTION OF THE DRAWINGS

FIG. A1 is a product data sheet for SG81 glass.

FIG. B1 shows a typical pigment curve illustrating the relative strength of UVA.

FIG. B2 illustrates the erythema action curve for UVB.

FIG. B3 illustrates combined erythema/pigment curves for UVA and UVB.

FIG. E1 illustrates the spectral irradiance characteristics of certain glass and phosphor combinations.

FIG. E2 is a raw data table for the graph of FIG. E1.

FIG. E3 is the sunlamp exposure table for the glass and phosphor combinations of FIGS. E1 and E2.

FIG. E4 is a comparison of the spectral irradiance characteristics of the combination referred to with respect to FIG. E1 and a standard lime glass, using a phosphor combination of the present invention. (6% UVB, 94% UVA)

FIG. E5 provides the raw data table for a phosphor combination of the present invention.

FIG. E6 provides the sunlamp exposure table for a phosphor combination of the present invention.

FIG. P1 shows the transmission curve of a phosphor useful in the present invention.

FIG. P2 shows the transmission curve of a phosphor useful in the present invention.

FIG. P3 shows the transmission curve of a phosphor useful in the present invention.

FIG. P4 illustrates a comparison of normalized melanogenesis, between a standard glass and one embodiment of a glass incorporating features of the present invention; using the above-described phosphor. FIG. P4 illustrates significantly increased transmission characteristics for the glass of the present invention using the above-described phosphor, particularly in the UVB range, and more particularly in the range of 283 to 305 nm.

FIG. P5 illustrates a comparison of Normalized Erythema curve, between a standard glass and one embodiment of a glass incorporating features of the present invention, using the above-described phosphor. FIG. P5 also illustrates significantly increased transmission characteristics for the glass of the present invention using the above-described phosphor, particularly in the UVB range, and more particularly in the range of 283 to 305 nm.

FIG. P6 illustrates a comparison of the graphs of FIGS. P4 and P5.

FIG. P7 illustrates the normalized spectral output for both a standard glass and a glass incorporating features of the present invention, using the above-referenced phosphor.

DETAILED DESCRIPTION OF THE INVENTION

The ultraviolet fluorescent lamp of the present invention generally comprises a glass or bulb that is formed with very pure sand and reduced level of impurities, such as, for example, iron and iron oxide. The bulb is provided with a phosphor, preferably a mixture of phosphors, that when used in conjunction with the glass of the present invention allows radiant energy in the UVB region, and preferably in the range of approximately 283-305 nm, to be transmitted with reduced levels of attenuation.

In a sun-tanning application, this glass and phosphor mix, when evaluated in terms of sensitivity factors, provides an enhanced response in the UVB region heretofore not seen nor recognized. (FIGS. P4-P6).

Glass (Bulb)

Various embodiments of the present disclosure relate to a glass for transmission of UV, and in particular to a glass with improved transmission in the UVB region. In order to reduce the damaging effects of solarization that are common with UV glass applications, the formation of glass of the present invention uses very pure sand together with low amounts of iron and iron oxide.

Soda Lime glass contains silica (silicon dioxide ($SiO_2$)), soda (sodium carbonate $Na_2CO_3$), or potash, (potassium carbonate, $K_2CO_3$), and lime (calcium oxide, CaO). Other elements such as iron and manganese may be added to adjust the color or other characteristics of the glass.

Typical soda lime glass does not transmit appreciable amounts of light at wavelengths lower than 400 nm, which means that ordinary glass cannot be used to transmit ultraviolet light. The absorption of UV radiation is an effect of the impurities present in the silica raw material and/or the presence of compounds used in glass manufacture as decolorizing or fining agents. Such compounds can radically change the transmittance characteristics of glass. Cerium, for example, absorbs UV radiation while iron absorbs infrared radiation. Early glass was quite green due to iron impurities in the sand used. Even today some glass has a greenish tint, caused by iron impurities in the sand used as a raw material.

It has been known that iron absorbs infrared radiation. We have also found that iron absorbs UV radiation at a level such that its presence in the soda lime glass in excessive amounts prevents the use of such glass in the present invention but that a limited amount of iron is beneficial for the functioning of the novel combination of glass and phosphors of this disclosure.

In one embodiment, the glass incorporating features of the present invention comprises, for example, soda lime glass that is formed using very pure sand and lower levels of impurities. For example, in one embodiment, the glass comprises less than 0.055% of iron in terms of $Fe_2O_3$, which is optionally carried as an impurity in the glass. In a preferred embodiment, a range of iron impurity in the glass is between 0.0450% and 0.0080%, by weight. This particular composition of glass has improved transmission characteristics in the UVB range. No cerium is added to the glass.

In alternate embodiments, other suitable glass and phosphor combinations can be used that provide improved transmission characteristics in the UVB range.

Table 1 below illustrates a comparison and analysis of a glass ("SOL GLASS") with an iron concentration in the range of 0.0450% to 0.008% to other glasses used in similar applications. As can be seen, when compared to the other glasses in this study, there is improved transmission using the SOL glass in the UVB range, particularly below approximately 330 nm.

TABLE 1

| Glass | SOL Glass | LT Higher Transmission | Lt Stand Magnesium | Sylvania SG81 |
|---|---|---|---|---|
| Fe2O3 Content (%) | 0.008–0.045 | 0.0120 | 0.030 | 0.0550 |
| Wavelength | Transmission | | | |
| 270 | 8.33 | 2.35 | 0.31 | 1.00 |
| 280 | 33.60 | 10.52 | 2.95 | 3.00 |
| 290 | 58.04 | 26.88 | 13.09 | 11.00 |
| 300 | 74.22 | 49.05 | 34.81 | 31.00 |
| 310 | 81.93 | 67.12 | 57.06 | 54.00 |
| 320 | 86.29 | 79.00 | 73.20 | 75.00 |
| 330 | 88.66 | 85.70 | 82.29 | 85.00 |
| 340 | 89.60 | 88.78 | 86.37 | 90.00 |
| 350 | 90.13 | 90.29 | 88.36 | 91.00 |
| 360 | 90.37 | 90.93 | 89.27 | 91.00 |
| 370 | 90.45 | 91.10 | 89.56 | 91.00 |
| 380 | 90.47 | 91.16 | 89.56 | 91.00 |
| 390 | 90.60 | 91.35 | 89.98 | 91.00 |
| 400 | 90.84 | 91.37 | 90.36 | 91.00 |

Phosphor

Embodiments of the present disclosue utilize a UVA phosphor which, when used in conjunction with the disclosed glasses, provides increased UV output in the UVB range, particularily in the range of 283-305 nm, as illustrated in FIGS. P4 and P5.

In one embodiment a UVA phosphor, such as for example a fluorescent lamp phosphor composed of strontium borate: Europium ($SrB_4O_7$: Eu), is used to coat the glass incorporating features of the present invention in a known or suitable fashion. One phosphor of this type is known as NP802 sold by NICHIA Corporation (Tokyo, Japan). Other UVA phosphors may be used. (see for example P1, P2, P3) The use of this type of UVA phosphor, in combination with the glass of the present invention, produces higher output in the UVB region, while in a standard glass, it has been found that the UVB output in this range is attenuated, due to the glass.

One example of a skin tanning fluorescent lamp construction utilizing a phosphor combination is found in U.S. Pat. No. 4,499,403 to Leppelmeir et al., filed on Sep. 6, 1979, the disclosure of which is incorporated herein and made a part hereof. An example of a UV lamp for accelerated exposure test on polymers is found in U.S. Pat. No. 4,859,903 to Minematu, et al., filed on Mar. 2, 1988, the disclosure of which is incorporated herein and made a part hereof.

FIG. P4 illustrates a comparison of normalized melanogenesis, between a standard glass and one embodiment of a glass incorporating features of the present invention; using the above-described phosphor.

FIG. P5 illustrates a comparison of Normalized Erythema, between a standard glass and one embodiment of a glass incorporating features of the present invention, using the above-described phosphor.

Both FIGS. P4 and P5 illustrate significantly increased transmission characteristics for the glass of the present invention using the above-described phosphor, particularly in the UVB range, and more particularly in the range of 283 to 305 nm.

FIG. P6 illustrates a comparison of the graphs of FIGS. P4 and P5.

FIG. P7 illustrates the normalized spectral output for both a standard glass and a glass incorporating features of the present invention, using the above-referenced phosphor.

EXAMPLE 1

In a preferred embodiment, and in order to intensify the ultraviolet wavelength coverage and transmission in the UVB region, and in particular the region between approximately 283 and 305 nm, a soda lime glass was formed with an amount of iron that is less than 0.055% by weight, and preferably in the range of 0.0450 to 0.008% by weight. A phosphor combination is used on the glass that comprises approximately 94% by weight of a UVA phosphor, such as for example Nichia phosphor NP802, and approximately 6% by weight of a UVB phosphor, such as for example Nichia phosphor NP803 or other UVB radiating phosphors.

FIG. E1 illustrates the spectral irradiance characteristics of certain glass and phosphor combinations. FIG. E2 is a raw data table for the graph of FIG. E1, while FIG. E3 is the sunlamp exposure table for the combination. FIG. E4 is a comparison of the spectral irradiance characteristics of the combination referred to with respect to FIG. E1 and a standard lime glass, using a phosphor combination of the present invention. (6% UVB, 94% UVA) FIGS. E5 and E6 provide the raw data table and sunlamp exposure table, respectively, for phosphor combination of the present invention By creating a soda lime glass with minimized iron impurities, the use of a UVA phosphor will provide improved transmission in the UVB region. The unique glass of the present invention provides for use of the UVB output region of a more resistant UVA phosphor, not heretofore seen. In essence, the phosphor combination, being primarily UVA, acts as a different phosphor, providing a broadband output with a peak in the UVA region and tail in the UVB region. When multiplied by a sensitivity factor, there is a higher output and impact on tanning in the UVB region, as illustrated by the graphs in FIGS. P1-P6. Thus, even though the spectral irradiance curve of FIG. E1 does not appear to perform well in the UVB region, multiplication by the sensitivity factor in terms of tanning ability shows a much higher impact on tanning and skin response to exposure when using the unique glass of the present invention with the particular phosphor mixture.

It should be understood that the foregoing description is only illustrative of the invention. Various alternatives and modifications can be devised by those skilled in the art without departing from the invention. Accordingly, the present invention is intended to embrace all such alternatives, modifications and variances.

The invention claimed is:

1. A florescent lamp comprising a low iron content glass bulb and containing a mixture of at least one phosphor selected from the group consisting of UVA phosphors and at least one phosphor selected from the group consisting of UVB phosphors and having spectral transmission of at least 50% throughout the range of 290 to 400 nm.

2. The lamp of claim 1 where the UVA phosphor is a strontium borate:europium phosphor.

3. The lamp of claim 1 comprising at least one UVA phosphor and at least one UVB phosphor where the ratio of the UVA phosphor to the UVB phosphor is about 94 to 6.

4. The lamp of claim 1 where the ratio of the UVA phosphor to the UVB phosphor is in the range of from about 92 to 8 and 96 to 4.

5. The lamp of claim 1 where the ratio of the UVA phosphor to the UVB phosphor is in the range of from about 90 to 10 to 97.5 to 2.5.

6. The lamp of claim 1 where the $Fe_2O_3$ content of the glass is below about 0.055% by weight.

7. The lamp of claim 1 where the $Fe_2O_3$ content of the glass is in the range of from about 0.008 to about 0.045% by weight.

8. The lamp of claim 1 where the $Fe_2O_3$ content of the glass is in the range of from about 0.01 to about 0.04% by weight.

9. The lamp of claim 1 where the $Fe_2O_3$ content of the glass is in the range of from about 0.02 to about 0.03% by weight.

* * * * *